(12) United States Patent
Kudo

(10) Patent No.: US 8,801,255 B2
(45) Date of Patent: Aug. 12, 2014

(54) ENDOSCOPE

(71) Applicant: Olympus Medical Systems Corp., Tokyo (JP)

(72) Inventor: Akira Kudo, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/861,431

(22) Filed: Apr. 12, 2013

(65) Prior Publication Data

US 2013/0265798 A1 Oct. 10, 2013

Related U.S. Application Data

(63) Continuation of application No. PCT/JP2012/076809, filed on Oct. 17, 2012.

(30) Foreign Application Priority Data

Oct. 27, 2011 (JP) ................. 2011-236389

(51) Int. Cl.
| | | |
|---|---|---|
| *A61B 1/06* | (2006.01) | |
| *A61B 3/00* | (2006.01) | |
| *F21V 5/00* | (2006.01) | |
| *G02B 6/06* | (2006.01) | |
| *G02B 15/02* | (2006.01) | |
| *G03B 29/00* | (2006.01) | |

(52) U.S. Cl.
USPC ........... 362/574; 362/572; 362/575; 600/101; 600/104; 600/108; 600/109; 600/110; 600/112; 600/129; 600/160; 600/178; 600/179

(58) Field of Classification Search
USPC ......... 600/110, 111, 112, 146, 178, 101, 104, 600/108, 109, 129, 160, 179; 362/572, 574, 362/575
See application file for complete search history.

(56) References Cited

U.S. PATENT DOCUMENTS

| | | | | |
|---|---|---|---|---|
| 5,429,529 A | * | 7/1995 | Hashizawa et al. | ........ 439/607.5 |
| 5,609,561 A | * | 3/1997 | Uehara et al. | ................. 600/112 |
| 6,036,636 A | * | 3/2000 | Motoki et al. | ................ 600/146 |
| 6,371,907 B1 | * | 4/2002 | Hasegawa et al. | ............ 600/146 |

(Continued)

FOREIGN PATENT DOCUMENTS

| | | | | |
|---|---|---|---|---|
| JP | 2002-051971 | | 2/2002 | |
| JP | 2005-077858 | | 3/2003 | |
| JP | 2006068057 | A * | 3/2006 | |
| JP | 2009-022588 | | 2/2009 | |

*Primary Examiner* — Thomas A Hollweg
(74) *Attorney, Agent, or Firm* — Scully, Scott, Murphy & Presser, P.C.

(57) ABSTRACT

An endoscope includes: a distal end rigid portion that configures a distal end portion of an insertion portion of an endoscope and has a through hole; an LED ceramic substrate including an LED light source mounted on a distal end side thereof, and arranged in the through hole so as to emit light from the through hole; an LED cable configured to be inserted in the insertion portion of the endoscope and to supply electric power to the LED light source; a ceramic cutout portion that configures a proximal end side of the LED ceramic substrate, and allows a conductive pattern for electrically connecting the LED light source and the LED cable to be exposed from inside the LED ceramic substrate and connected to the LED cable; and a reinforcement member having rigidity and fixed to the LED ceramic substrate and configured to cover the ceramic cutout portion.

7 Claims, 6 Drawing Sheets

(56) References Cited

U.S. PATENT DOCUMENTS

| | | | |
|---|---|---|---|
| 6,488,619 B1* | 12/2002 | Miyanaga | 600/179 |
| 6,692,431 B2* | 2/2004 | Kazakevich | 600/178 |
| 8,333,694 B2* | 12/2012 | Kudo et al. | 600/178 |
| 2003/0050534 A1* | 3/2003 | Kazakevich | 600/178 |
| 2006/0183977 A1* | 8/2006 | Ishigami et al. | 600/179 |
| 2007/0191684 A1* | 8/2007 | Hirata | 600/179 |
| 2008/0300457 A1* | 12/2008 | Hosaka et al. | 600/110 |
| 2009/0030274 A1* | 1/2009 | Goldfarb et al. | 600/106 |
| 2009/0177038 A1* | 7/2009 | Yashiro et al. | 600/132 |
| 2010/0188493 A1* | 7/2010 | Kanzaki et al. | 348/75 |
| 2010/0261961 A1* | 10/2010 | Scott et al. | 600/111 |
| 2011/0230722 A1* | 9/2011 | Kudo et al. | 600/178 |
| 2011/0306834 A1* | 12/2011 | Schrader et al. | 600/112 |
| 2012/0002394 A1* | 1/2012 | Todd et al. | 362/13 |

* cited by examiner

US 8,801,255 B2

ENDOSCOPE

CROSS REFERENCE TO RELATED APPLICATION

This application is a continuation application of PCT/JP2012/076809 filed on Oct. 17, 2012 and claims benefit of Japanese Application No. 2011-236389 filed in Japan on Oct. 27, 2011, the entire contents of which are incorporated herein by this reference.

BACKGROUND OF THE INVENTION

1. Field of the Invention

The present invention relates to an endoscope provided with a light emitting device, as an illuminating section, at a distal end portion of an insertion portion.

2. Description of the Related Art

Endoscopes are widely used in medical fields and industrial fields. Targets to be diagnosed or observed through endoscopes are inside a living body or a plant. Therefore, a light source for illuminating a target to be observed is required when endoscopic observation is performed.

A common endoscope apparatus is provided with an endoscope, and a light source device as an external device of the endoscope. Illumination light emitted by the light source device is transmitted through a light guide inserted in the endoscope. The transmitted illumination light is emitted toward a target to be observed from an illumination window arranged at a distal end of an insertion portion.

In recent years, an endoscope has been proposed, which is provided with a light emitting device such as a light-emitting diode (LED) at a distal end portion of an insertion portion, instead of a combination of a light source device and a light guide fiber, and which directly illuminates a target to be observed with the light emitted by the light emitting device. As shown in FIG. 1, in addition to an LED light source unit 4 configuring an illuminating section, internal components such as an observation unit 5 and various fluid tubes 6 are attached to a distal end rigid member 3 configuring a distal end portion 2 of an endoscope 1. The LED light source unit 4 is configured by including an LED ceramic substrate 8 on which an LED light source 41 is mounted. In the endoscope 1, the size or the like of the LED ceramic substrate 8 configuring the LED light source unit 4 is limited.

In order to avoid interference between the LED ceramic substrate 8 and the observation unit 5, or interference between the LED ceramic substrate 8 and internal components, an escape portion 8a such as a step or a cutout is formed on the LED ceramic substrate 8.

In an LED unit assembling work as shown in FIG. 2, the LED light source unit 4 is assembled to an illumination disposing portion 11 as a recessed portion of a lens cover 10 fixed to the distal end rigid member 3. In an observation unit assembling work, the observation unit 5 is assembled to the distal end rigid member 3, as shown in FIG. 3.

SUMMARY OF THE INVENTION

An endoscope according to one aspect of the present invention includes: a distal end rigid portion that configures a distal end portion of an insertion portion of an endoscope and has a through hole; an LED ceramic substrate including an LED light source mounted on a distal end side thereof, the LED ceramic substrate being arranged in the through hole so as to emit light from the through hole; an LED cable configured to be inserted in the insertion portion of the endoscope and to supply electric power to the LED light source; a ceramic cutout portion that configures a proximal end side of the LED ceramic substrate, the ceramic cutout portion allowing a conductive pattern for electrically connecting the LED light source and the LED cable to be exposed from inside the LED ceramic substrate and connected to the LED cable; and a reinforcement member having rigidity, the reinforcement member being fixed to the LED ceramic substrate and configured to cover the ceramic cutout portion.

BRIEF DESCRIPTION OF THE DRAWINGS

FIGS. 1 to 3 relate to prior arts, in which FIG. 1 illustrates an LED light source unit, an observation unit and internal components which are provided at a distal end portion of an endoscope.

FIG. 2 illustrates an LED unit assembling work.

FIG. 3 illustrates an observation unit assembling work.

FIGS. 4-10 relate to an embodiment of the present invention, in which FIG. 4 illustrates a configuration of a distal end portion of an endoscope provided with an LED light source unit according to the present invention.

FIG. 5 illustrates a configuration of the LED light source unit.

FIG. 6 illustrates an LED unit assembling work in which the LED light source unit is assembled to a distal end rigid portion.

FIG. 7 illustrates an observation unit assembling work in which the observation unit is assembled to the distal end rigid portion to which the LED light source unit is assembled.

FIG. 10 illustrates a configuration and working of a protection frame.

DETAILED DESCRIPTION OF THE PREFERRED EMBODIMENT(S)

Hereinafter, an embodiment of the present invention will be described with reference to drawings.

Figure 1:
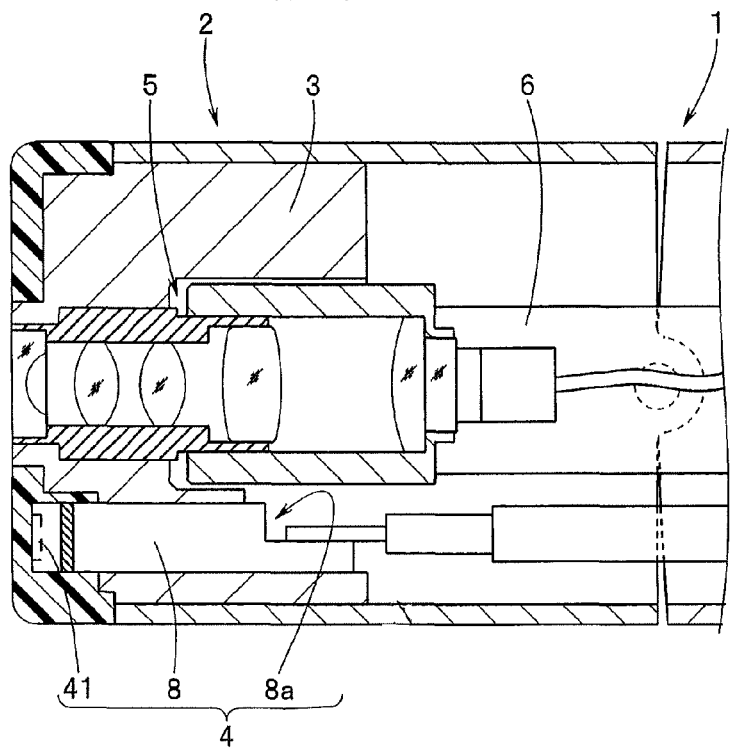
Figure 2:
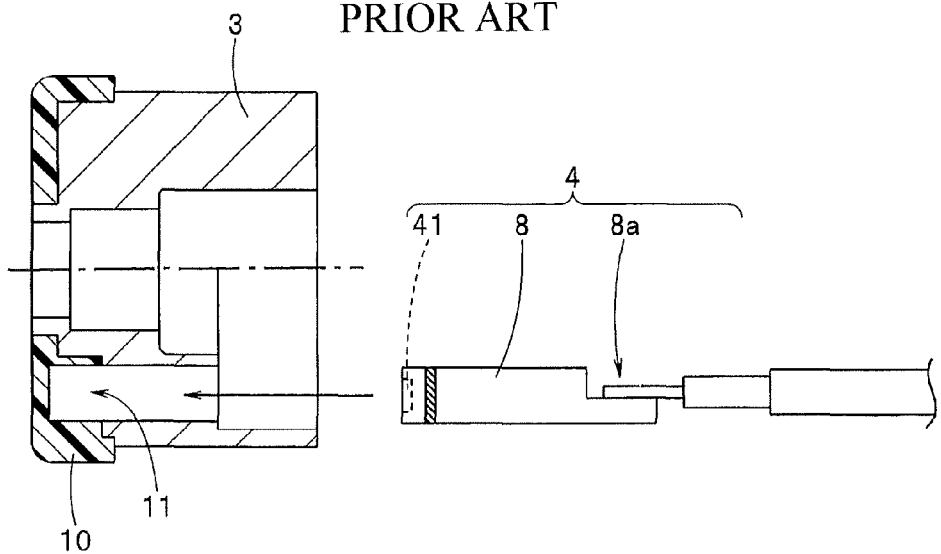
Figure 3:
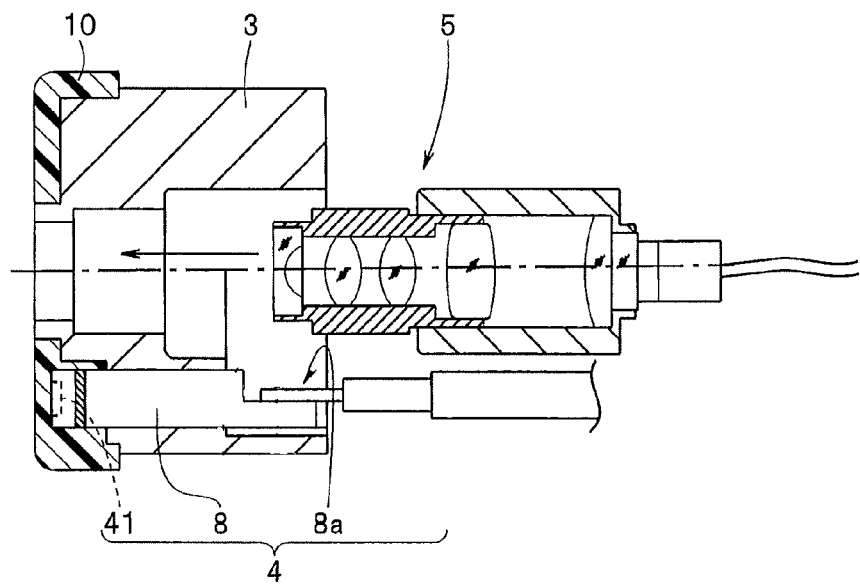
Figure 4:
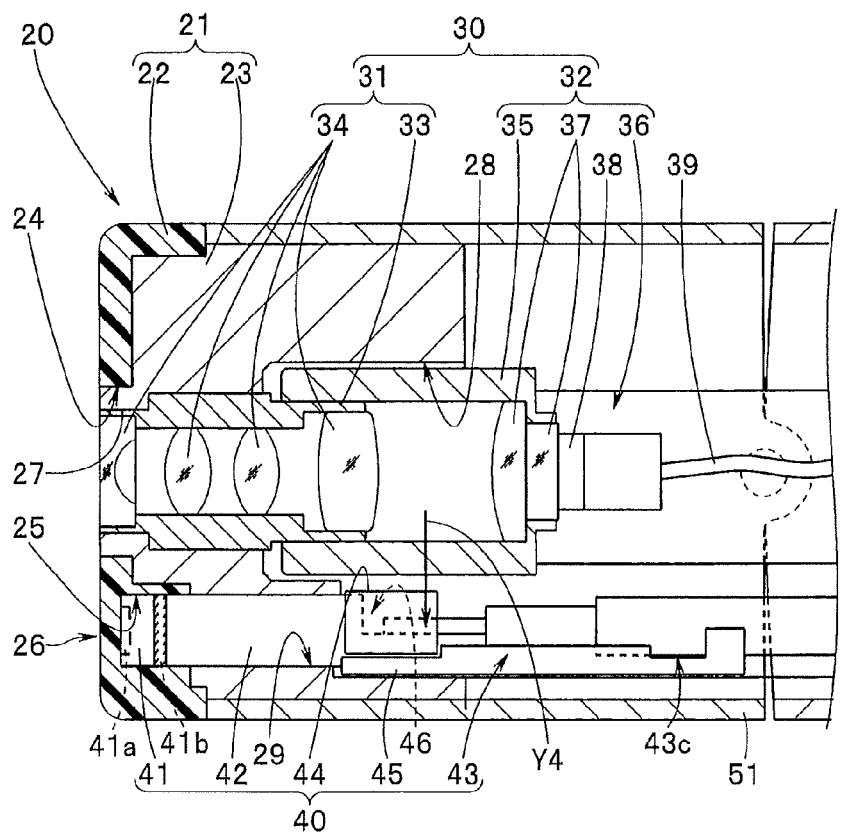

A configuration of a distal end portion of an insertion portion of an endoscope will be described with reference to FIG. 4.

A distal end portion 21 of an insertion portion of an endoscope 20 is configured by including a distal end cover 22 and a distal end rigid portion 23. The distal end cover 22 is made of an insulation member and the distal end rigid portion 23 is made of a metal member such as stainless steel.

The distal end cover 22 is made of transparent resin member (made of polysulphone, for example) and formed in a cylindrical shape. On the distal end cover 22, a rigid member through hole 24, a nozzle through hole, and a treatment instrument through hole are formed. The distal end rigid portion 23 is disposed in the rigid member through hole 24. A cleaning nozzle, not shown, is disposed in the nozzle through hole. The treatment instrument through hole configures a treatment instrument insertion hole, not shown.

The reference numeral 25 represents an LED light source disposing hole. The LED light source disposing hole 25 is a recessed portion in which an LED light source 41 provided at the distal end portion of an LED light source unit 40 is disposed. The front face of the LED light source disposing hole 25 is configured as an illumination window 26.

The central axis of the rigid member through hole 24, the central axis of the nozzle through hole, the central axis of the treatment instrument through hole, and the central axis of the LED light source disposing hole 25 are respectively parallel to the central axis of the distal end cover 22.

The distal end rigid portion 23 includes a projected portion 27. The projected portion 27 is inserted and disposed in the rigid member through hole 24. An observation unit through hole 28, an LED light source unit through hole 29, air-feeding/water-feeding through hole (not shown), and the treatment instrument through hole (not shown) are formed at the distal end rigid portion 23. An observation unit 30 is disposed in the observation unit through hole 28. The LED light source unit 40 is disposed in the LED light source unit through hole 29.

The distal end side of the air-feeding/water-feeding through hole communicates with the nozzle through hole. An air-feeding tube and a water-feeding tube, which are not shown, are connected to the proximal end side of the air-feeding/water-feeding through hole, through a tube ferrule (not shown). The treatment instrument through hole configures a treatment instrument insertion hole. The distal end side of the treatment instrument through hole communicates with the treatment instrument through hole of the distal end cover 22. The proximal end side of the treatment instrument through hole is connected with a treatment instrument channel tube, not shown, through a channel ferrule (not shown). The central axis of the observation unit through hole 28, the central axis of the LED light source unit through hole 29, the central axis of air-feeding/water-feeding through hole, and the central axis of the treatment instrument through hole are parallel to the central axis of the distal end rigid portion 23.

The observation unit 30 is provided with a lens unit 31 and an image pickup apparatus 32. The lens unit 31 is configured by including a lens frame 33, and a plurality of optical members. The optical members include a plurality of optical lenses 34, and the like arranged in the lens frame 33. The lens frame 33 is made of a metal material which has excellent rigidity and corrosion-resistance, such as stainless steel.

On the other hand, the image pickup apparatus 32 is configured by including an image pickup frame 35, an image pickup section 36, and a cover lens 37. The image pickup section 36 is configured by a circuit substrate, not shown, on which an image pickup device 38 and electronic components are mounted. The image pickup device 38 is a CCD, a CMOS, or the like. The cover lens 37 is provided on the light-receiving surface side of the image pickup device 38. The reference numeral 39 represents a signal cable and the signal cable is extended toward the operation portion. Also the image pickup frame 35 is made of a metal material which has excellent rigidity and corrosion-resistance, such as stainless steel.

Figure 5:
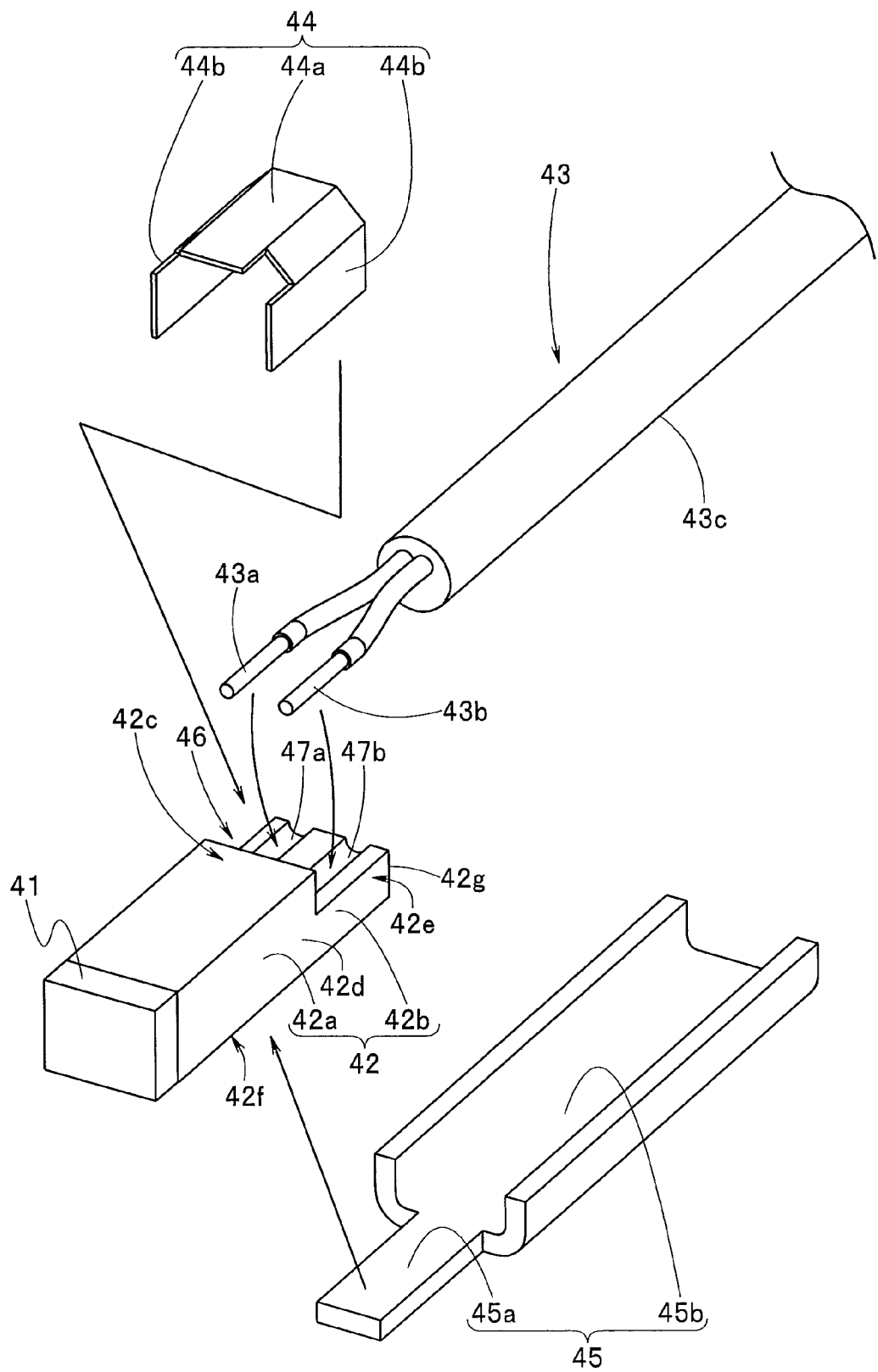

The configuration of the LED light source unit 40 is described with reference to FIGS. 4 and 5.

The LED light source unit 40 is configured by including the LED light source 41, an LED ceramic substrate (hereinafter, shortly referred to as LED substrate) 42, an LED cable 43, a reinforcement member 44, and a heat-radiation plate 45. The LED substrate 42 is a ceramic substrate which has high heat conductivity and insulation property.

The LED light source 41 includes, on one surface side thereof, one or a plurality of LEDs 41a as a light-emitting portion. The LED light source 41 includes, on the other surface side thereof, a conductive portion 41b.

The LED substrate 42 has a rectangular parallelepiped shape, for example. The LED substrate 42 has, on the distal end side thereof, an LED light source holding portion (not shown). The conductive portion 41b side of the LED light source 41 is disposed in the LED light source holding portion. Inside the LED substrate 42, a conductive pattern for electrically connecting the LED light source 41 and the LED cable 43 is provided. The LED cable 43 for supplying electric power is inserted in the insertion portion of the endoscope 20 to be guided to the distal end portion 21.

A ceramic cutout portion (hereinafter shortly referred to as cutout portion) 46 is formed on the proximal end side of the LED substrate 42. The LED substrate 42 on which the cutout portion 46 is formed has an L-shape including a first rectangular parallelepiped portion 42a and a second rectangular parallelepiped portion 42b. The first rectangular parallelepiped portion 42a configures the distal end side and the second rectangular parallelepiped portion 42b configures the proximal end side. The first rectangular parallelepiped portion 42a is configured so as to have a predetermined thickness dimension. On the other hand, the second rectangular parallelepiped portion 42b is so formed as to have a thickness dimension thinner than that of the first rectangular parallelepiped portion 42a by the cutout portion 46.

The cutout portion 46 allows conductive patterns 47a, 47b to be exposed. A first core line 43a of the LED cable 43 is arranged in the first conductive pattern 47a exposed by the cutout portion 46 and electrically connected thereto, with soldering, not shown, for example. A second core line 43b of the LED cable 43 is electrically connected to the second conductive pattern 47b in a similar manner with soldering.

Note that the first conductive pattern 47a, the second conductive pattern 47b, the first core line 43a, and the second core line 43b may be provided in plural numbers depending on the number of the LEDs 41a provided to the LED light source 41.

In addition, in the present embodiment, the LED substrate 42 has a rectangular parallelepiped shape. However, the LED substrate 42 may have a prism shape, the cross-sectional shape of which is pentagon, hexagon, etc., or a cylindrical shape, the cross-sectional shape of which is round, ellipse, etc.

The reinforcement member 44 is formed in a square U-shape with a predetermined thickness dimension. The reinforcement member 44 is made of a metal material having rigidity, such as stainless steel, for example. The reinforcement member 44 is integrally adhered and fixed to the LED substrate 42 using insulating adhesive, for example.

The reinforcement member 44 is configured by including a lid surface 44a and a pair of adhesive side surfaces 44b. The inner surface of the lid surface 44a is adhered and fixed onto a cutout-side one surface 42c of the first rectangular parallelepiped portion 42a of the LED substrate 42. In addition, the inner surfaces of the pair of adhesive side surfaces 44b are adhered and fixed to a pair of first side surfaces 42d each of which is adjacent to the cutout side one surface 42c, and adhered and fixed to a pair of second side surfaces 42e of the second rectangular parallelepiped portion 42b, which are the same surfaces as the first side surfaces 42d.

An insulative encapsulation resin or adhesive is filled in a space formed by the reinforcement member 44 which covers the cutout portion 46 and the second rectangular parallelepiped portion 42b of the LED substrate 42. The reinforcement member 44 and the second rectangular parallelepiped portion 42b are integrally configured with the encapsulation resin or the adhesive. The insulative encapsulation resin or the adhesive prevents electric contact between the reinforcement member 44 and the core lines 43a, 43b.

The heat-radiation plate 45 is formed with a metal material having high heat conductivity such as copper, or aluminum, or formed with a heat-conductive member configured by a material such as graphite that has an anisotropic nature in a heat-conductive direction. The thickness, width, and length of the heat-radiation plate 45 is appropriately set by taking the external dimension of the distal end portion 21 of the endoscope 1, the heat radiation capacity, and the like into consideration. In the present embodiment, the cross-sectional shape of the heat-radiation plate 45 is a square U-shape.

The heat-radiation plate 45 includes an adhesive portion 45a and a cable fixing portion 45b. The adhesive portion 45a is brought into close contact with and fixed to the other surface 42f which is rear surface of the cutout-side one surface 42c of the first rectangular parallelepiped portion 42a configuring the LED substrate 42, for example. The cable fixing portion 45b is previously protruded from a proximal end surface 42g of the LED substrate 42. The proximal end of the cable fixing portion 45b is configured so as to be disposed in a distal-most bending piece 51. A cable main body 43c of the LED cable 43 is adhered and fixed to the cable fixing portion 45b. As a result, the unstable motion of the distal end part of the LED cable 43 can be prevented without increasing the length of the endoscope rigid portion.

Note that the cross-sectional shape of the heat-radiation plate 45 is not limited to the square U-shape, but may be formed in a desired solid shape such as a plate shape, an L-shape, a U-shape, a semi-circular shape, or a box shape.

The lid surface 44a and the adhesive side surfaces 44b of the reinforcement member 44 are thus adhered and fixed to the cutout-side one surface 42c and the pair of first side surfaces 42d of the first rectangular parallelepiped portion 42a of the LED substrate 42, and adhered and fixed to the pair of second side surfaces 42e of the second rectangular parallelepiped portion 42b, to cover the cutout portion 46 formed on the proximal end side of the LED substrate 42. According to this configuration, it is possible to prevent such a failure that a force in the Y4 direction is accidentally applied to the cutout portion 46.

Figure 6:
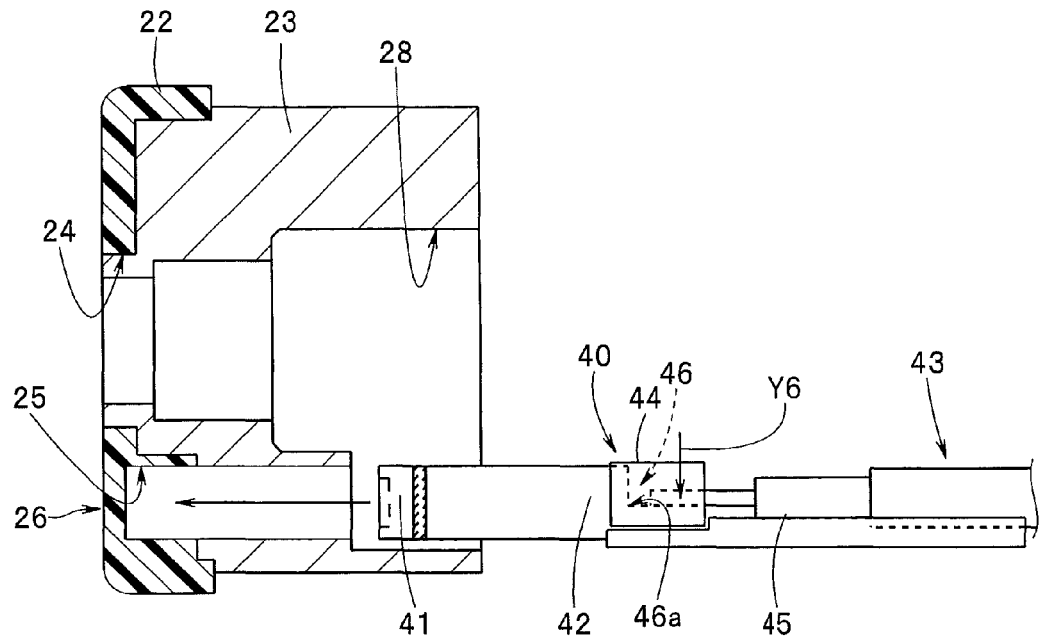

As a result, in the LED unit assembling work shown in FIG. 6, when the LED light source 41 of the LED light source unit 40 is assembled into the LED light source disposing hole 25 of the distal end cover 22, through the LED light source unit through hole 29 of the distal end rigid portion 23, a force in the arrow Y6 direction is prevented from accidentally acting on the cutout portion 46. Therefore, during the LED assembling work, it is possible to prevent breakage of the LED substrate 42 due to stress concentrating at the corner 46a of the cutout portion 46.

Figure 7:
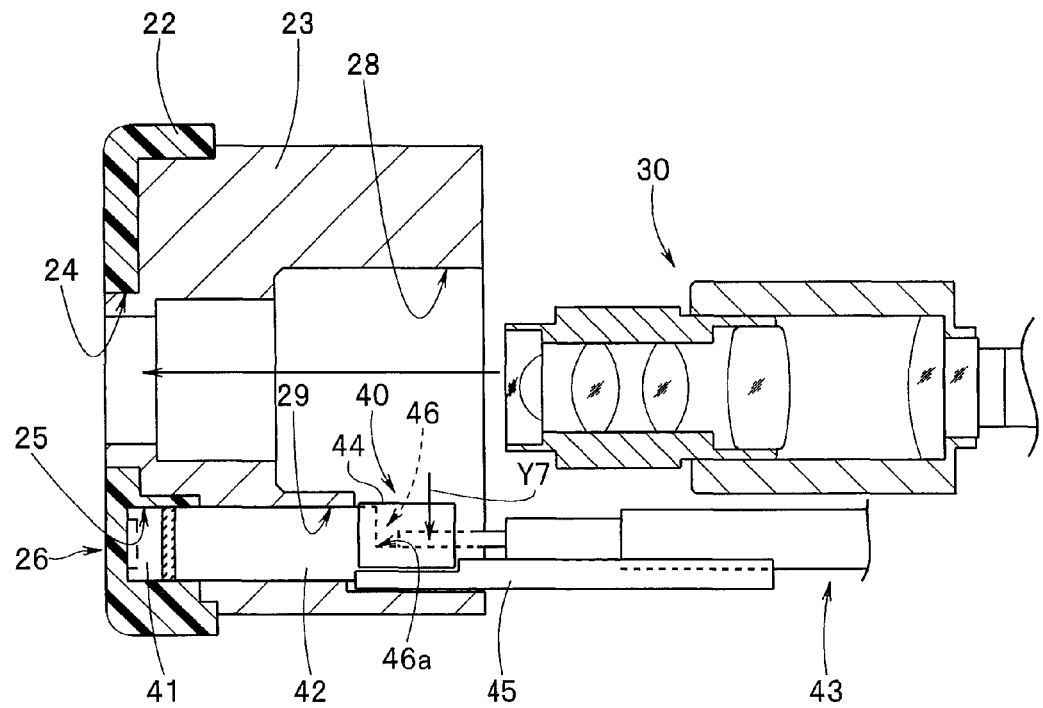

In addition, in the observation unit assembling work after the LED unit assembling work, when the observation unit 30 is assembled to the distal end rigid portion 23 as shown in FIG. 7, a force in the arrow Y7 direction is prevented from accidentally acting on the cutout portion 46. Therefore, during the observation unit assembling work, it is possible to prevent breakage of the LED substrate 42 due to stress concentrating at the corner 46a of the cutout portion 46.

The cutout portion 46 of the LED substrate 42 is thus covered with the reinforcement member 44 made of metal member which has rigidity and which is formed in a predetermined thickness dimension, thereby capable of preventing breakage of the LED substrate 42 due to stress concentrating at the corner 46a of the cutout portion 46, without increasing the thickness dimension of the LED substrate 42. As a result, it is possible to reduce the diameter of the distal end portion.

Figure 8A:
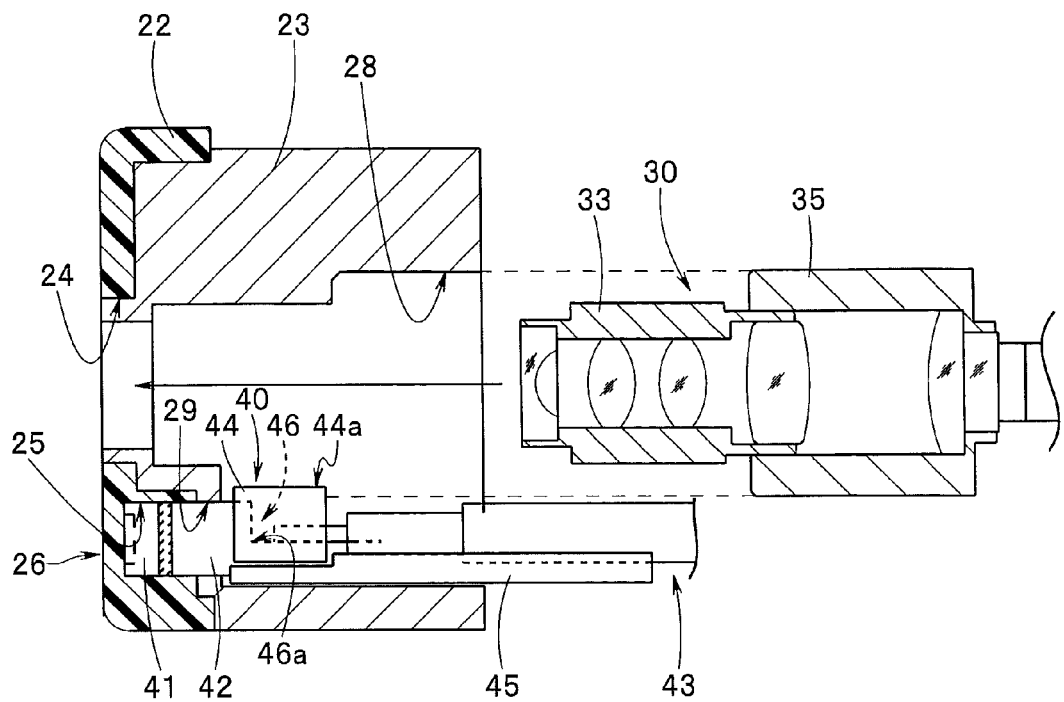
FIG. 8A illustrates a relationship between the distal end rigid portion to which the LED light source unit is assembled and the observation unit including an image pickup frame having a large diameter.
Figure 8B:
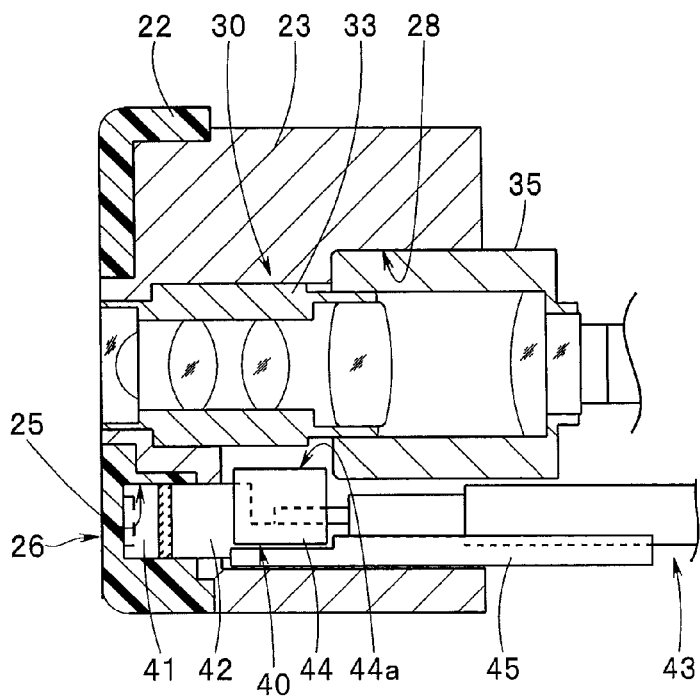
FIG. 8B illustrates a state where the observation unit in FIG. 8A is assembled to the distal end rigid portion.

As shown in FIGS. 8A, 8B, when the observation unit 30 having the image pickup frame 35, diameter of which is larger than that of the lens frame 33, and the LED light source unit 40 are assembled to the distal end rigid portion 23, the reinforcement member 44 of the LED light source unit 40 is disposed in the forward direction of the distal end rigid portion 23 than the image pickup frame 35 of the observation unit 30, and the outer circumferential portion of the lid surface 44a of the reinforcement member 44 covering the cutout portion 46 of the LED light source unit 40 is brought close to the lens frame 33 and arranged in the center direction of the distal end rigid portion 23.

According to this configuration, the LED light source unit 40 is assembled to the central axis direction of the distal end rigid portion 23 so as to be located at a position where the LED cable 43 of the LED light source unit 40 does not interfere with the image pickup frame 35 of the observation unit 30. As a result, it is possible to prevent breakage of the LED substrate 42 and reduce the diameter of the distal end.

Furthermore, the cable main body 43c of the LED cable 43 is adhered and fixed to the heat-radiation plate 45 protruded from the proximal end surface of the LED substrate 42. As a result, during the assembling work, it is possible to surely prevent the force in the arrow Y6 direction and the force in the arrow Y7 direction from acting on the cutout portion 46 due to unstable motion of the cable 43.

Figure 9A:
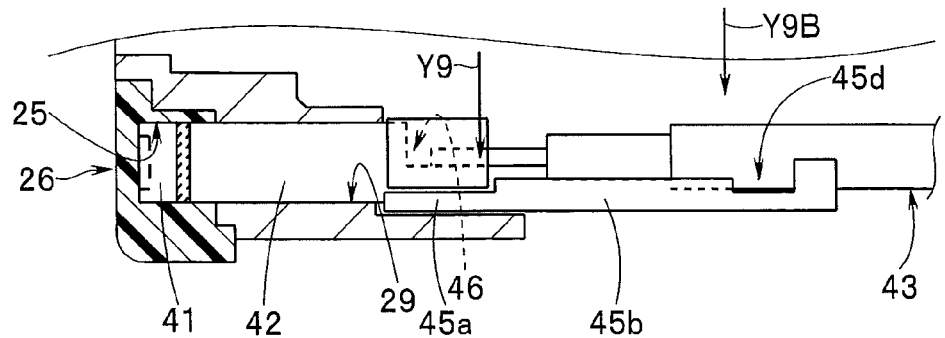
FIG. 9A illustrates a configuration and working of a heat-radiation plate having a cutout portion.
Figure 9B:
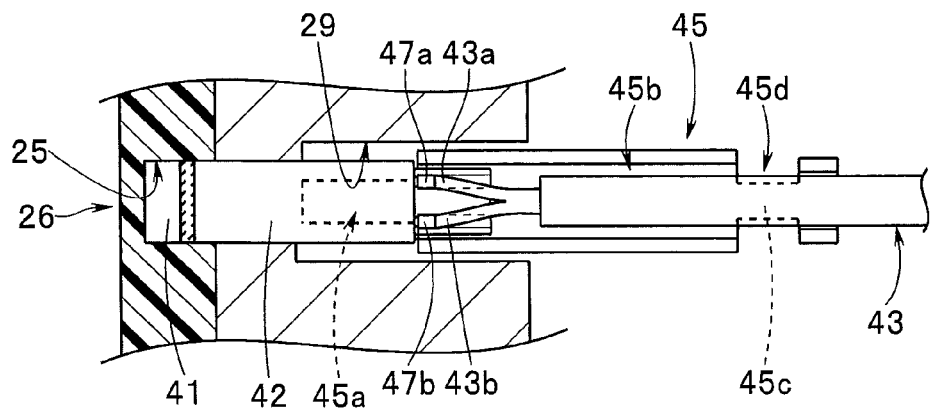
FIG. 9B illustrates the LED light source unit having a heat-radiation plate, which is seen from the direction of the arrow 9B in FIG. 9A.

Note that a cutout 45d is provided for configuring a deform portion 45c at a cable fixing portion 45b of the heat-radiation plate 45, as shown in FIGS. 9A and 9B.

According to this configuration, in the case where the LED cable 43 extended from the cable fixing portion 45b moves unstably, the deform portion 45c deforms before a force in the arrow Y9 direction acts on an adhered and fixed portion at which the first core line 43a and the first conductive pattern 47a are adhered and fixed and an adhered and fixed portion at which the second core line 43b and the second conductive pattern 47b are adhered and fixed, thereby relieving the force in the arrow Y9 direction. As a result, it is possible to prevent such a failure that the force in the Y9 direction accidentally acts on the cutout portion 46.

Figure 10:
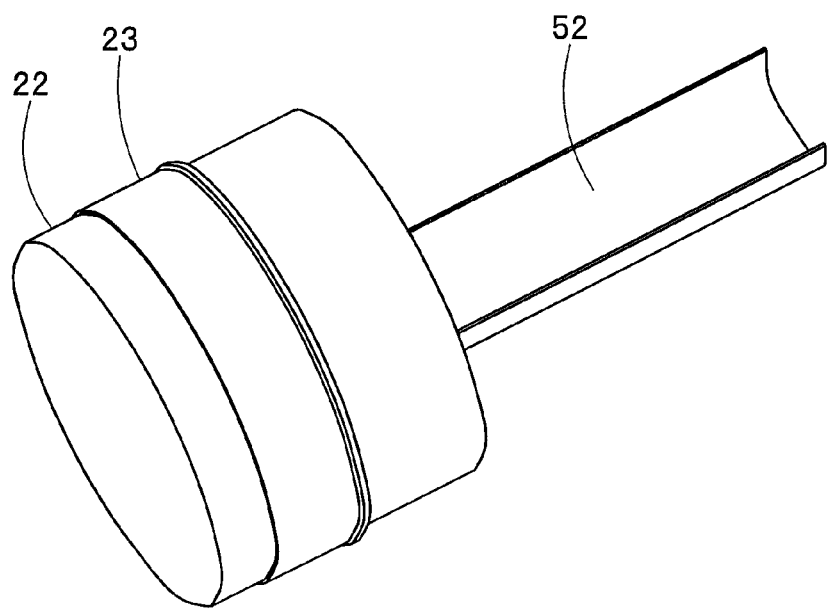

In addition, as shown in FIG. 10, for example, a square U-shaped protection frame 52 made of stainless steel may be provided in a standing manner by making use of a vacant space of the distal end rigid portion 23. The protection frame 52 is provided so as to be opposed to the cable fixing portion 45b of the heat-radiation plate 45. The protection frame 52 provided in a standing manner at the distal end rigid portion 23 is arranged in the distal-most bending piece 51.

According to this configuration, the LED cable 43 is arranged between the protection frame 52 and the cable fixing portion 45b without adhering and fixing the LED cable 43 to the cable fixing portion 45b, thereby capable of surely preventing the unstable motion of the LED cable 43.

Note that the present invention is not limited to the above-described embodiment, but various modifications are possible without departing from the gist of the present invention.

What is claimed is:
1. An endoscope comprising:
a distal end rigid portion that constitutes a distal end portion of an insertion portion of an endoscope and has a through hole;
an LED ceramic substrate including an LED light source mounted on a distal end side thereof, the LED ceramic substrate being arranged in the through hole so as to emit light from the through hole;

an LED cable configured to be inserted in the insertion portion of the endoscope and to supply electric power to the LED light source;

a ceramic cutout portion that constitutes a proximal end side of the LED ceramic substrate, the ceramic cutout portion allowing a conductive pattern for electrically connecting the LED light source and the LED cable to be exposed from inside the LED ceramic substrate and connected to the LED cable; and a reinforcement member made of metal and having rigidity, the reinforcement member being fixed to the LED ceramic substrate by insulating adhesive and configured to cover the ceramic cutout portion.

2. The endoscope according to claim 1, wherein the LED ceramic substrate is arranged in the through hole such that the ceramic cutout portion is oriented to a central axis of the insertion portion of the endoscope.

3. The endoscope according to claim 2, further comprising a heat-radiation plate having a cable fixing portion at which the LED cable is arranged and fixed, and a deform portion formed by providing a cutout at a predetermined position of the cable fixing portion.

4. The endoscope according to claim 1, wherein the reinforcement member is a thin plate member, which is formed in a square U-shape to have a pre-determined thickness dimension with a lid surface and a pair of adhesive side surfaces.

5. The endoscope according to claim 1, wherein the LED ceramic substrate is a rectangular parallelepiped shape, and is formed to have an L-shape including a first rectangular parallelepiped portion having a predetermined thickness dimension and constituting the distal end side of the LED ceramic substrate and a second rectangular parallelepiped portion having the ceramic cutout portion and formed so as to have a thickness dimension thinner than the thickness dimension of the first rectangular parallelepiped portion.

6. The endoscope according to claim 5, wherein the first rectangular parallelepiped portion has a cutout-side surface to which a lid surface of the reinforcement member is fixed and a pair of first side surfaces to which a pair of adhesive side surfaces of the reinforcement member are fixed, and the second rectangular parallelepiped portion has a pair of second side surfaces to which the pair of adhesive side surfaces of the reinforcement member are fixed.

7. The endoscope according to claim 1, wherein one of an insulative encapsulation resin or adhesive is filled in a space formed by the ceramic cutout portion and the reinforcement member covering the ceramic cutout portion.

* * * * *